United States Patent [19]

Asano et al.

[11] Patent Number: 5,532,943

[45] Date of Patent: Jul. 2, 1996

[54] PARTICLE ANALYZING APPARATUS AND METHOD THEREFOR

[75] Inventors: Kaoru Asano; Yukimi Ikekita, both of Kobe, Japan

[73] Assignee: TOA Medical Electronics Co., Ltd., Kobi, Japan

[21] Appl. No.: 174,249

[22] Filed: Dec. 28, 1993

[30] Foreign Application Priority Data

Dec. 28, 1992 [JP] Japan ................................. 4-359893

[51] Int. Cl.$^6$ ................................................. G01N 33/49
[52] U.S. Cl. ........................ 364/555.000; 364/552.000; 382/133.000
[58] Field of Search .................................. 364/497, 554, 364/555, 551.010, 552.000; 356/39; 382/6, 133–134

[56] References Cited

U.S. PATENT DOCUMENTS

| | | | |
|---|---|---|---|
| 4,661,913 | 4/1987 | Wu et al. ................................. | 364/555 |
| 4,706,207 | 11/1987 | Hennessy et al. ....................... | 364/555 |
| 4,741,043 | 4/1988 | Bacus ..................................... | 364/416 |
| 5,187,673 | 2/1993 | Carver, Jr. et al. ..................... | 364/555 |
| 5,333,244 | 7/1994 | Harashima ......................... | 364/413.16 |

FOREIGN PATENT DOCUMENTS

3-131756  5/1991  Japan.

*Primary Examiner*—Ellis B. Ramirez
*Assistant Examiner*—Craig Stevens Miller

[57] ABSTRACT

A particle analyzing apparatus includes a particle detector for measuring each of many particles to obtain at least one kind of data for each particle, a conversion unit for converting the obtained data into distribution data, a data base memory for storing reference distribution data relative to the distribution data, and a calculating unit for calculating the degree of similarity $\delta$ of the distribution data with respect to the reference distribution data.

25 Claims, 5 Drawing Sheets

PARTICLE ANALYZING APPARATUS AND METHOD THEREFOR

BACKGROUND OF THE INVENTION

1. Field of the Invention

The present invention relates to a particle analyzing apparatus and a method therefor, and more particularly to an apparatus that can express in a value to what extent the distribution data obtained as a result of the particle analysis is similar to the reference distribution data. The apparatus is useful for analyzing various particles in blood.

2. Description of the Related Art

Conventional particle analyzing apparatus include one that provides measured data concerning a plurality of particles to classify the particles measured based on the difference in such measured data. For example, when hemocytes are measured as the above particles, a sample in which hemocytes are suspended is successively supplied to a particle detection unit. Every time particles are detected in the detection unit, the unit generates two kinds of data items X1 and X2. Data items X1 and X2 obtained in each particle are converted into distribution data in a characteristic parameter space. In the process, the distribution data provides two-dimension scattergram data F (X1, X2) in which data items X1 and X2 form coordinate axes respectively. Hemocytes are classified into granulocytes, lymphocytes, and monocytes on the basis of the two-dimension scattergram.

In the above particle analyzing apparatus, a distribution pattern on the scattergram allows classifying whether or not the sample is normal or abnormal. In addition, detailed investigation of the distribution pattern enables presuming the identity of disease. Thus, a case collection in which typical scattergrams in each disease are described is provided to users of the particle analyzing apparatus. Users compare scattergrams obtained with the particle analyzing apparatus with scattergrams described in the case collection, thereby finding similarities therebetween to use them as test data.

Such method involving much dependence on the subjective judgment of man, however, demands a considerable time in determining the identity of each disease. Besides, the result of judgment by this method is also ambiguous. Thus it is hard to say that the method is effective. Consequently there is need for an analyzing apparatus and a method therefor that facilitates a quantitative and simple analysis of the probability of each disease by representing in a value the degree of similarity between the scattergram obtained in the particle analyzing apparatus and the scattergram in the typical cases of disease.

On the other hand, the particle analyzing apparatus require a control for assuring that the apparatus themselves are operated in a favorable condition, or the quality control thereof. Conventionally, in the quality control, a parameter is determined that constitutes a goal in each measurement item in the apparatus. The accuracy control of the apparatus involves inspecting the fluctuation in the parameter. Any attempt of improving the precision in the quality control (a capacity of detecting that they are operated in a favorable condition), however, requires a larger number of parameters. Along with the multiplication of the number of dimensions from the two to three-dimensions in the distribution data obtained by the particle analyzing apparatus, the number of parameters to be controlled increases with the result that controlling such parameters demands more trouble and time.

Consequently, there is need for a particle analyzing apparatus that facilitates an accuracy control with more simple method and in shorter time.

In addition, when a particle analyzing apparatus is manufactured, it is necessary to evaluate distribution data obtained from the particle analyzer thus manufactured as to whether or not the data has reproducibility and stability (as to whether the same distribution data can be obtained when the same sample is analyzed many times). In other words, it is necessary to conduct a performance evaluation as to whether the particle analyzing apparatus can be shipped as a product. Conventionally the performance evaluation was conducted along with the quality control. Thus the evaluation required much trouble and time.

Consequently there is need for a particle analyzing apparatus that facilitates the performance evaluation with a simple method in a short time.

As an aside, Japanese laid-open patent No. HEI 3-131756 describes an automatic classifying device for blood cells for detecting and analyzing immature blood cells (abnormal blood cells) by using a hierarchic network through the input of form parameter, a concentration parameter, a color tone parameter and a texture parameter.

SUMMARY OF THE INVENTION

The present invention is to provide a particle analyzing apparatus that can satisfy the above requirements and a method using the apparatus.

According to the invention, there is provided a particle analyzing apparatus comprising, particle detection means for measuring each of particles to obtain at least one kind of data of each particle, conversion means for converting the obtained data into distribution data, data base storing means for storing reference distribution data relative to the distribution data, and calculation means for calculating the degree of similarity $\delta$ of the distribution data with the reference distribution data.

Furthermore the above calculating means enables calculating the degree of similarity with respect to data in the predetermined region of the above distribution data F (X1, X2, - - - Xn) and the above reference distribution data G (X1, X2, - - - Xn) utilizing Mathematical Expression 3

[Mathematical Expression 3]

$$\delta = \frac{\sum_{X1} \ldots \sum_{Xn} F(X1,X2\ldots Xn) \cdot G(X1,X2\ldots Xn)}{\left(\sum_{X1} \ldots \sum_{Xn} |F(X1,X2\ldots Xn)|^2 \cdot \sum_{X1} \ldots \sum_{Xn} |G(X1,X2\ldots Xn)|^2\right)^{1/2}}$$

In addition, it is possible to use the above reference distribution data as a representative distribution data (hemocyte distribution data) in a certain disease by replacing the particle with hemocyte. In addition, it is possible to use the reference distribution data as reference distribution data for quality control of the particle analyzing apparatus or reference distribution data for quality evaluation.

A method for analyzing particles according to the present invention comprises, the steps of, measuring each of particles to obtain at least one kind of data of each particle, converting the obtained data into distribution data, and calculating degree of similarity $\delta$ of the distribution data with reference distribution data relative to the distribution data.

In the step of calculating the degree of similarity δ, it is possible to calculate the above degree of similarity based on Mathematical Expression 4 with respect to the above distribution data F (X1, X2 - - - Xn) and the above reference distribution data G (X1, X2 - - - Xn).

[Mathematical Expression 4]

$$\delta = \frac{\sum_{X1} \ldots \sum_{Xn} F(X1,X2 \ldots Xn) \cdot G(X1,X2 \ldots Xn)}{\left( \sum_{X1} \ldots \sum_{Xn} |F(X1,X2 \ldots Xn)|^2 \cdot \sum_{X1} \ldots \sum_{Xn} |G(X1,X2 \ldots Xn)|^2 \right)^{1/2}}$$

In accordance with the apparatus and the method of the present invention, when the distribution data is obtained, the degree of similarity δ of the distribution data relative to the reference distribution data can be obtained as a value by using the distribution data thus obtained and the reference distribution data.

Use of the distribution data of a certain disease as the reference distribution data provides a probability that the sample is suffering from the disease, a data of diagnosis from the calculated degree of similarity δ.

On the other hand, use of the reference distribution data for quality control of the particle analyzing apparatus or the reference distribution data for quality evaluation allows quality control and evaluation of the apparatus with knowledge as to whether the apparatus is in normal condition from the degree of similarity δ and as well as to what extent the apparatus is deviated from the normal condition.

BRIEF DESCRIPTION OF THE DRAWINGS

By way of example reference is made to the accompanying drawings in which.

DETAILED DESCRIPTION OF THE PREFERRED EMBODIMENTS

The present invention will be detailed in accordance with illustrative embodiments, but the present invention is not limited by them.

Referring to an embodiment shown in FIGS. 1 and 2, the present apparatus will be explained.

Figure 1:
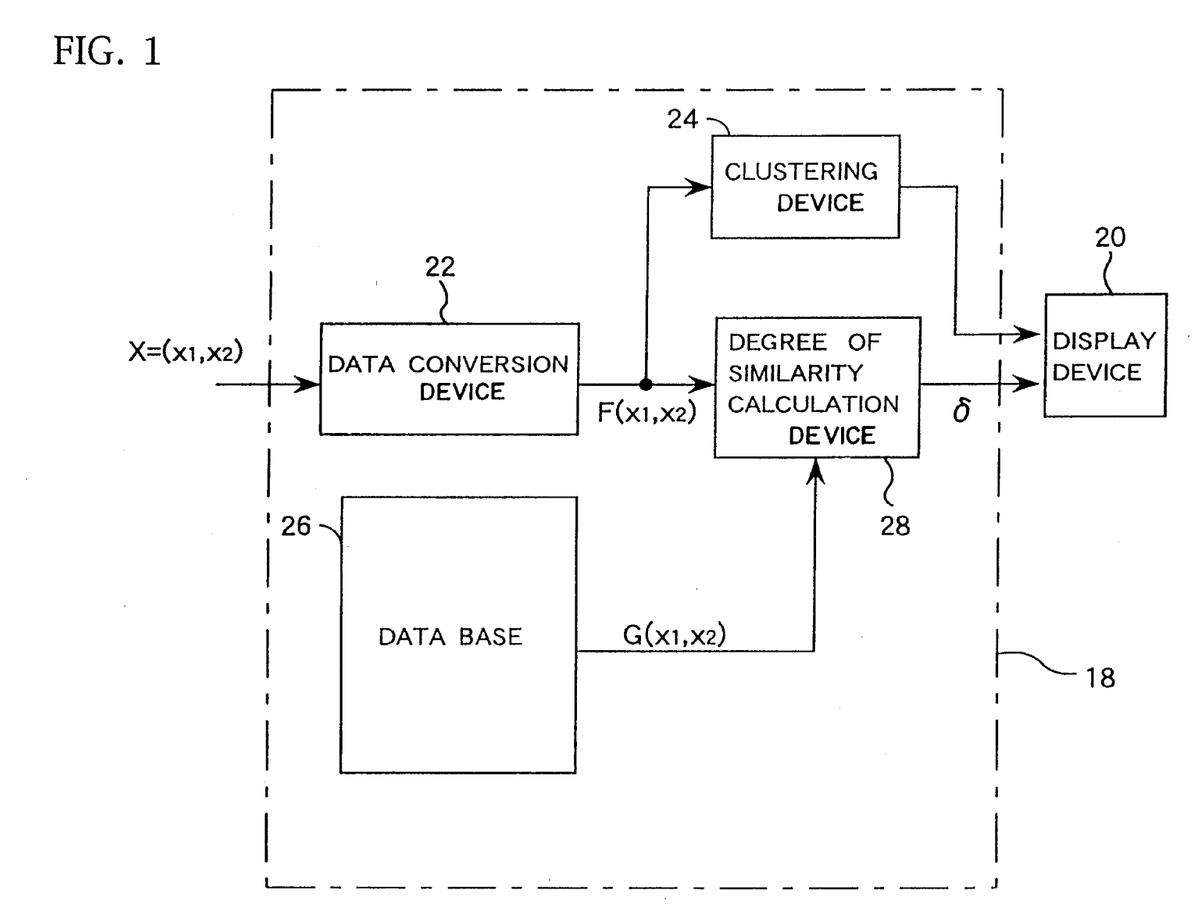
FIG. 1 is a block diagram of a data analyzing device 18 in accordance with a particle analyzing apparatus of the present invention.
Figure 2:
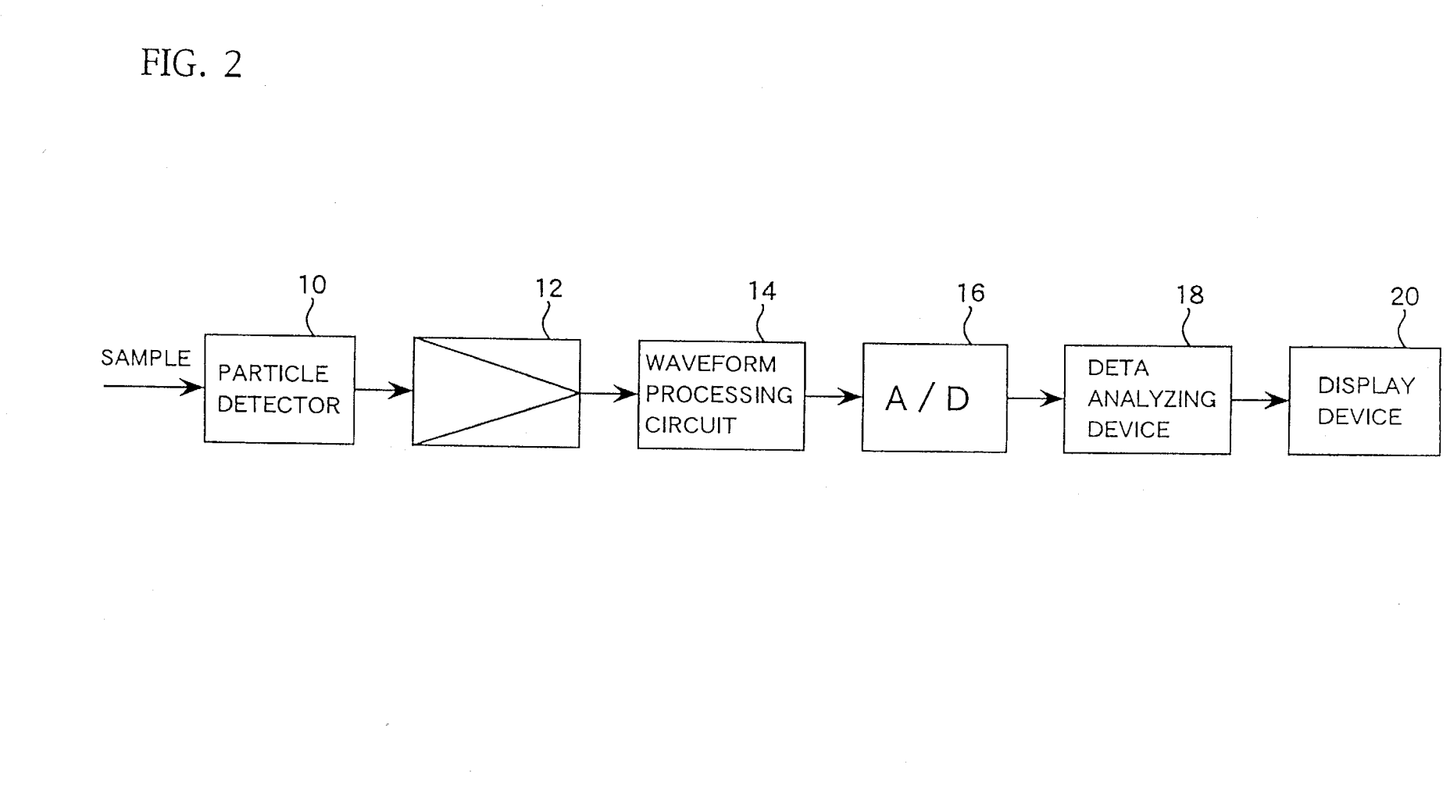
FIG. 2 is a block diagram of one preferred embodiment of the present invention.

As shown in FIGS.1 and 2, the present apparatus comprises a particle detector 10, an amplifier circuit 12 which amplifies a signal, a waveform processing circuit 14 which processes a waveform of the signal, an A/D converter 16 which gives a digital signal, a data analyzing device 18 and a display device.

The data analyzing device 18 comprises a data conversion means 22, a clustering means 24, a data base memory means 26 and a degree of similarity calculation means 28.

The particle detection means of the present invention usually comprises the particle detector 10, the amplifier circuit 12, the waveform processing circuit 14 and the A/D converter 16.

The particle detection means of the present invention includes any known detectors which can measure each of very fine particles to obtain at least one kind of data of each particle. Typical examples include a flowcytometer and a detector providing a fine hole. The flowcytometer detects a signal of scattered light or fluorescence generated in each particle. In the detector providing a fine hole, a direct current and a high frequency current are simultaneously supplied to the fine hole thereby enabling the detector to detect a signal based on a change in the impedance of direct current and a signal based on a change in the impedance of high frequency (Automated Hemotology Analyzer NE Series, produced by TOA MEDICAL ELECTRONICS CO., LTD., is this type).

To the particle detector 10 is supplied e.g. a blood sample which is conventionally pretreated (i.e. diluted and hemolyzed) and suspends leukocytes. When each particle such as leukocytes contained in the blood sample passes through the detector 10, plural kinds of signals are generated. For example, the flowcytometer can detect a signal of scattered light or fluorescence generated in each particle, while the detector providing a fine hole can detect a signal based on a change in direct current impedance as well as a signal based on a change in a high frequency impedance.

After plural kinds of signals detected by the particle detector 10 are amplified by the amplifier circuit 12, the waveform processing circuit 14 processes the waveform of the signals, the A/D converter 16 converts them into digital signals.

The digital signals transmitted from the A/D converter 16 is supplied to the data analyzing device 18. The detected signal of particle that has been converted into a digital signal is analyzed by this data analyzing device 18. The result of analysis is utilized to classify the particle and displayed in the display device 20.

This data analyzing device 18 comprises, for example, a microcomputer. A means as shown in FIG. 1 is realized with software. Incidentally a digital signal entered into this data analyzing device are classified into two kinds; signal X1 defined by digitalizing a signal utilizing a change in direct current impedance thus obtained and signal X2 defined by digitalizing a signal utilizing a change in a high frequency impedance.

The data analyzing device 18 provides the data conversion means 22, which converts obtained data into distribution data. Namely, the data conversion means 22 converts signals X1 and X2 generated in each particle into distribution data F (X1, X2) of characteristics parameter space.

Figure 3:
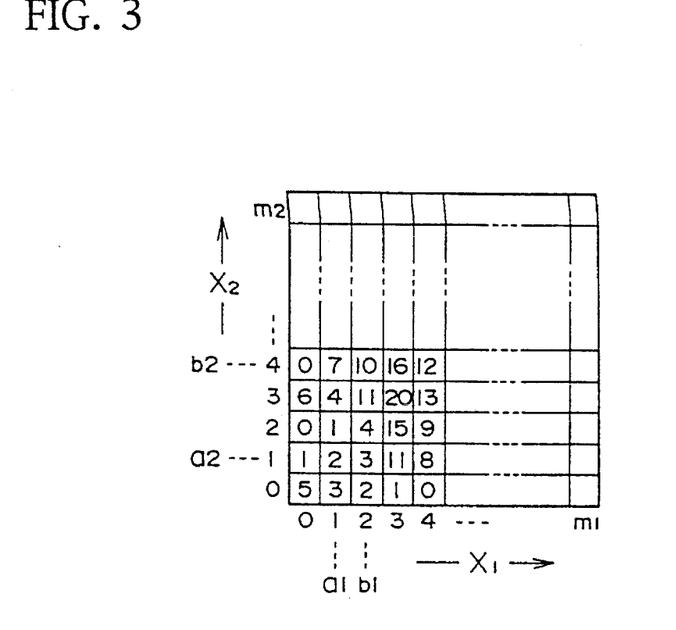
FIG. 3 is a view showing a content of a memory provided in a data conversion means 22 in accordance with the present invention.

In other words, data conversion means 22 provides a memory having a parameter X1 comprising a total of m1 +1 channels (ranks) and a parameter X2 comprising a total of m2 +1 channels (ranks) as shown in FIG. 3. Consequently this memory is divided into basic elements of [(m+1) X (m2 +1)].

Every time signals X1 and X2 are entered to the data conversion means 22, the memory value of basic elements corresponding to the size of X1 and the size of X2 that have been entered is increased. Consequently when signals X1 and X2 corresponding to all the particles are entered into the data conversion means 22, there is shown that two particles are present in all the particles, each of the two particles having parameter X1 which assumes 1 and parameter X2 which assumes 1 if F (1, 1) assumes 2.

The distribution data F (X1, X2) obtained by the data conversion means 22 is supplied to the clustering means 24, and the clustering means 24 clusters (classify), for example, the distribution data under monocytes, granules and lymphocytes.

Figure 4:
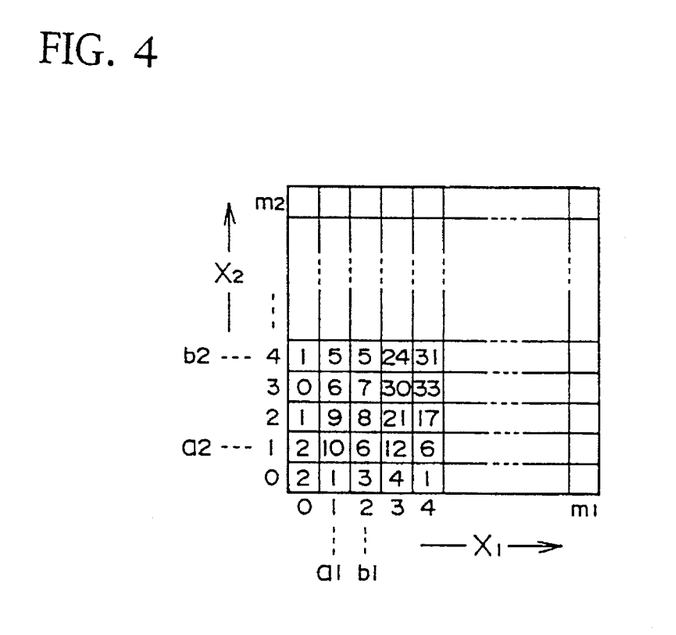
FIG. 4 is a view showing a content of a data base memory means in accordance with the present invention.

This data analyzing device 18 provides the data base memory means 26 which stores reference distribution data G (X1, X2) that constitute the standard. FIG. 4 shows an example of this reference distribution data G (X1, X2). The construction of the data base memory means 26 is identical to the construction of the data conversion means 22. For example, G (1, 1) indicates that 10 out of all the particles have parameter X1 assuming 1 as well as parameter X2 assuming 1.

As this reference distribution data, for example, a representative two-dimension distribution data in a certain disease or two-dimension distribution data (two-dimension distribution data for quality control) can be utilized which is obtained by analyzing a certain material for quality control when a particle controller is in a normal operation.

The degree of similarity calculation means 28 calculates a degree of similarity $\delta$ of the distribution of the two-dimension distribution data F (X1, X2) with respect to the reference distribution data G (X1, X2) by comparing the two-dimension distribution data F (X1, X2) obtained at the data conversion means 22 with the reference distribution data G (X1, X2) of the data base memory means 26. The display device 20 displays the result of the calculation.

The degree of similarity calculation means 28 calculates the degree of similarity concretely in Mathematical. Expression 5.

[Mathematical Expression 5]

$$\delta = \frac{\sum_{X1=a1}^{b1} \sum_{X2=a2}^{b2} F(X1,X2) \cdot G(X1,X2)}{\left( \sum_{X1=a1}^{b1} \sum_{X2=a2}^{b2} |F(X1,X2)|^2 \cdot \sum_{X1=a1}^{b1} \sum_{X2=a2}^{b2} |G(X1,X2)|^2 \right)^{1/2}}$$

in Mathematical Expression 5, a region for calculating the degree of similarity $\delta$ is set to channel a1 to b1 with respect to the parameter X1 and to channel a2 to b2 with respect to the parameter X2. The region needs not to be all the spaces of characteristics parameter (from channel 0 to channel m1 in parameter X1 and from channel 0 to channel m2 in parameter X2). The region can be set to the most appropriate region depending on the purpose. For example, when the region where data is not distributed can be preliminarily determined, the degree of similarity $\delta$ can be calculated only with respect to the scope outside of the region.

When the degree of similarity $\delta$ is calculated based on the distribution data F (X1, X2) in FIG. 3 and FIG. 4 and the reference distribution data G (X1, X2), the following result is produced. Incidentally as shown in FIG. 3 and 4, the above calculation is performed with a1=channel 1, b1=channel 2, a2=channel 1 and b2=channel 4 being set.

Mathematical Expression 6 represents the numerator in Mathematical Expression 5.

[Mathematical Expression 6]

$$\sum_{X1=1}^{2} \sum_{X2=1}^{4} F(X1,X2) \cdot G(X1,X2) = F(1,1) \cdot G(1,1) + F(2,1) \cdot G(2,1)$$
$$+ F(1,2) \cdot G(1,2) + F(2,2) \cdot G(2,2)$$
$$+ F(1,3) \cdot G(1,3) + F(2,3) \cdot G(2,3)$$
$$+ F(1,4) \cdot G(1,4) + F(2,4) \cdot G(2,4)$$
$$= 2 \cdot 10 + 3 \cdot 6$$
$$+ 1 \cdot 6 + 4 \cdot 8$$
$$+ 4 \cdot 6 + 11 \cdot 7$$
$$+ 7 \cdot 5 + 10 \cdot 5$$
$$= 265$$

[Mathematical Expression 7]

$$\sum_{X1=1}^{2} \sum_{X2=1}^{4} |F(X1,X2)|^2 = |F(1,1)|^2 + |F(2,1)|^2$$
$$+ |F(1,2)|^2 + |F(2,2)|^2$$
$$+ |F(1,3)|^2 + |F(2,3)|^2$$
$$+ |F(1,4)|^2 + |F(2,4)|^2$$
$$= 2^2 + 3^2$$
$$+ 1^2 + 4^2$$
$$+ 4^2 + 11^2$$
$$+ 7^2 + 10^2$$
$$= 316$$

Then Mathematical Expression 7 represents the first half of the denominator in Mathematical Expression 5. In the same manner Mathematical Expression 8 represents the latter half of the denominator.

[Mathematical Expression 8]

$$\sum_{X1=1}^{2} \sum_{X2=1}^{4} |G(X1,X2)|^2 = |G(1,1)|^2 + |G(2,1)|^2$$
$$+ |G(1,2)|^2 + |G(2,2)|^2$$
$$+ |G(1,3)|^2 + |G(2,3)|^2$$
$$+ |G(1,4)|^2 + |G(2,4)|^2$$
$$= 10^2 + 6^2$$
$$+ 9^2 + 8^2$$
$$+ 6^2 + 7^2$$
$$+ 5^2 + 5^2$$
$$= 416$$

Consequently the degree of similarity $\delta$ is given as $265/(316 \cdot 416)^{1/2} = 0.731$. Mathematical Expression 5 represents a correlative constant of the function F (X1, X2) and G (X1, X2). When the distribution data F (X1, X2) and the reference distribution data G (X1, X2) are similar to each other, or when $F(X1, X2) = K \cdot G(X1, X2)$ (wherein K is a constant), the degree of similarity $\delta$ assumes a maximum value 1. As the two distributions gradually becomes distant from each other (or as the similarity of the distributions between the two is lost), the value of $\delta$ becomes smaller and approaches to zero. In other words, the degree of similarity $\delta$ quantitatively represents the similarity of the two-dimension distribution.

The above phenomenon will be detailed theoretically hereinbelow. Analysis is made as to how Mathematical Expression 5 behaves relative to the change in the distribution. Data used in this analyzing apparatus is a digital signal given as a dispersion data. Assuming for simplicity that the distribution data and the reference distribution data are continuously distributed, Mathematical Expression 9 represents a degree of similarity $\delta$ with respect to the two-dimension distribution data.

[Mathematical Expression 9]

$$\delta = \frac{\iint f(x,y) g(x,y) dx dy}{\sqrt{\iint f(x,y)^2 dx dy} \sqrt{\iint g(x,y)^2 dx dy}}$$

For illustration, when a continuous one-dimension distribution is considered at the outset, the degree of similarity $\delta$ is represented by Mathematical Expression 10 (see page 11, "Image Processing Theory" written by Yasuhiro Doi and Shigeru Ando, published by Shokodo).

[Mathematical Expression 10]

$$\delta = \frac{\int f(x) \int g(x) dx}{\sqrt{\int f(x)^2 dx} \sqrt{\int g(x)^2 dx}}$$

When the original distribution function f(x) is given as a normal distribution N (m,σ), f(x) is represented by Mathematical Expression 11.

[Mathematical Expression 11]

$$f(x) = \frac{1}{\sqrt{2\pi}\ \sigma} \exp(-(x-m)^2/2\sigma^2)$$

Figure 5:
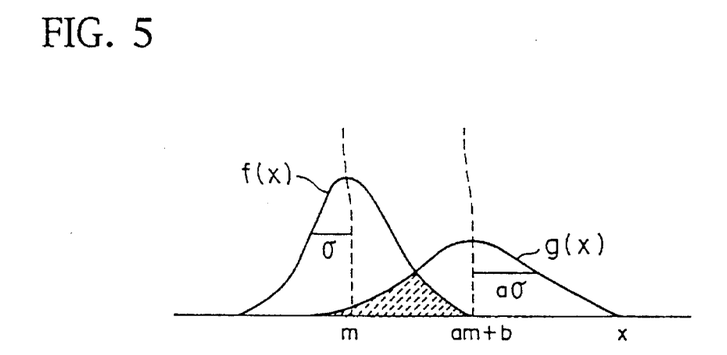
FIG. 5 is a view illustrating the relative constant of two one-dimension data items.

As for the above f (x), when a function in which σ is converted to aσ and m to am +b is set to g (x), the g (x) is a normal distribution N (am + b, $a^{2\sigma^2}$), and is represented by Mathematical Expression 12. (See FIG. 5.).pa

[Mathematical Expression 12]

$$g(x) = \frac{1}{\sqrt{2\pi}\ a\sigma} \exp(-(x-am-b)^2/2a^2\sigma^2)$$

Needless to say, the integral value of f (x) and g (x) in the range from the negative infinite to the positive infinite assumes 1.

Calculating the first half of the denominator of Mathematical Expression 10 by using Mathematical Expression 11 provides the result represented by Mathematical Expression 13.

[Mathematical Expression 13]

$$\int f(x)^2 dx = \int \frac{1}{\sqrt{2\pi}\ \sigma} \exp(-(x-m)^2/2\sigma^2) \cdot \frac{1}{\sqrt{2\pi}\ \sigma} \exp(-(x-m)^2/2\sigma^2) dx$$

$$= \frac{1}{2\sigma\sqrt{\pi}}$$

In the same manner, calculating the latter half of Mathematical Expression 10 with Mathematical Expression 12 provides the result represented by Mathematical Expression 14.

[Mathematical Expression 14]

$$\int g(x)^2 dx = \int \frac{1}{\sqrt{2\pi}\ a\sigma} \exp(-(x-am-b)^2/2a^2\sigma^2) \cdot \frac{1}{\sqrt{2\pi}\ a\sigma} \exp\left(\frac{-(x-am-b)^2}{2a^2\sigma^2}\right)$$

$$= \frac{1}{2a\sigma\sqrt{\pi}}$$

In the same manner, calculating the numerator of Mathematical Expression 10 with Mathematical Expressions 11 and provides the result represented by Mathematical Expression 15.

[Mathematical Expression 15]

$$\int f(x) g(x) dx = \int \frac{1}{\sqrt{2\pi}\ \sigma} \exp\left(\frac{-(x-m)^2}{2\sigma^2}\right) \cdot \frac{1}{\sqrt{2\pi}\ a\sigma} \exp\left(\frac{-(x-am-b)^2}{2a^2\sigma^2}\right) dx$$

$$= \frac{1}{2\pi a\sigma^2} \int \exp\left(-\frac{((a^2+1)(x-(a^2m+am+b)/(a^2+1))^2 + a^2(am+b-m)^2/(a^2+1))}{2a^2\sigma^2}\right) dx$$

Here C is defined as shown in Mathematical Expression 16.

[Mathematical Expression 16]

$$C = \exp(-((am+b-m)^2/2(a^2+1\sigma^2))$$

In such case, Mathematical Expression 17 can represent Mathematical Expression 15. Thus dispersion σ can be represented by Mathematical Expression 18.

[Mathematical Expression 17]

$$\int f(x)g(x)dx = \frac{C}{2\pi a \sigma^2} \int \exp\left(\frac{-(x-(a^2m+am+b)/(a^2+1))^2}{2a^2(a^2+1)^{-1}\sigma^2}\right) dx$$

$$= \frac{C}{\sqrt{2\pi}\ \sigma\sqrt{a^2+1}}$$

[Mathematical Expression 18]

$$\delta = \frac{\sqrt{2a}}{\sqrt{a^2+1}} \exp(-(am+b-m)^2/2(a^2+1)\sigma^2)$$

In the case of transfer, dispersion σ in g (x) relative to the original distribution data f(X) is the same as the counterpart in f (x) (a=1). In the case of m + b wherein the average value is shifted by b from f (x), Mathematical Expression 19 can represent the degree of similarity δ.

[Mathematical Expression 19]

$$\delta = \exp\left(-\frac{b^2}{4\sigma^2}\right)$$

Table 1 shows the relation between the amount of transfer b and the degree of similarity δ wherein m=100 and σ=10 are set. Table 1 shows that along with an increase in the amount of transfer b, the degree of similarity δ rapidly decreases.

TABLE 1

| b | δ |
|---|---|
| 0 | 1.000 |
| ±2 | 0.990 |
| ±5 | 0.939 |
| ±10 | 0.779 |
| ±15 | 0.570 |
| ±20 | 0.368 |

When the sensitivity changes, or when dispersion of g (x) relative to the original distribution data f (x) is given by aσ and the average value is given by am (b=0) (or f (x) multiplied by a), Mathematical Expression 20 can represent the degree of similarity δ.

[Mathematical Expression 20]

$$\delta = \frac{\sqrt{2a}}{\sqrt{a^2+1}} \exp(-(a-1)^2 m^2/2(a^2+1)\sigma^2)$$

In the manner, Table 2 shows the relation between the sensitivity a and the degree of similarity δ wherein m=100 and σ=10 are set. Table 2 shows that along with an increase in a from 1, the degree of similarity δ rapidly decreases.

TABLE 2

| a | δ | a | δ |
|---|---|---|---|
| 1.00 | 1.000 | | |
| 1.02 | 0.990 | 0.98 | 0.990 |
| 1.05 | 0.942 | 0.95 | 0.936 |
| 1.10 | 0.796 | 0.90 | 0.757 |
| 1.15 | 0.613 | 0.85 | 0.517 |
| 1.20 | 0.437 | 0.80 | 0.292 |

Then two-dimension distribution is considered hereinbelow. Mathematical Expression 9 can represent the degree of similarity δ. In this case, when the original distribution function is given as a normal distribution, Mathematical Expression 21 can represent function f (x). Here, it is based on a condition of X=(x, y). Even when K=σ² I(I is a unit queue) is established with an appropriate conversion of variables, the general properties of Mathematical Expression 21 is still maintained. Thus Mathematical Expression 22 represents Mathematical Expression 9.

[Mathematical Expression 21]

$$f(X) = \frac{1}{2\pi |K|^{-1/2}} \exp(-(X-m)K^{-1}(X-m)^T)$$

[Mathematical Expression 22]

$$f(x,y) = \frac{1}{2\pi\sigma^2} \exp\left(\frac{-((x-m_x)^2 + (y-m_y)^2)}{2\sigma^2}\right)$$

Figure 6:
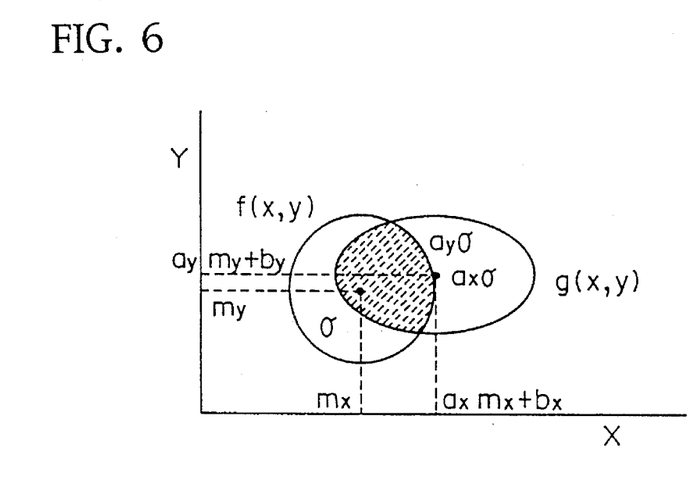
FIG. 6 is a view illustrating the relative constant of two two-dimension data items.

With respect to f (x, y), g (x, y) is given as a function in which data is converted; σ to $a_x\sigma$, $m_x$ to $a_x m_x + b_x$ in the X direction, and σ to $a_y\sigma$, $m_y$ to $a_y m_y + b_y$ direction. This is represented by Mathematical Expression 23 (see 5 FIG. 6).

[Mathematical Expression 23]

$$g(x,y) = \frac{1}{2\pi a_x a_y \sigma^2} \exp\left(-\frac{(x-a_x m_x - b_x)^2/a_x^2 + (y-a_y m_y - b_y)^2/a_y^2}{2\sigma^2}\right)$$

Needless to say, Mathematical Expression 24 is given as follows.

[Mathematical Expression 24]

$$\int\int_{-\infty}^{\infty} f(x,y)dxdy = 1 \quad \int\int_{-\infty}^{\infty} g(x,y)dxdy = 1$$

When Mathematical Expression 25 represents f (x, y), Mathematical Expression 26 is established.

[Mathematical Expression 25]

$$f(x,y) = f_1(x)F_2(y)$$

[Mathematical Expression 26]

$$\int\int f(x,y)\,dxdy = \int f_1(x)dx \cdot \int f_2(y)\,dy$$

Thus Mathematical Expression 27 represents the first half of the denominator in Mathematical Expression 9.

[Mathematical Expression 27]

$$\iint f(x,y)^2 dxdy = \iint \frac{1}{(2\pi\sigma^2)^2} \exp\left(-\frac{(x-m_x)^2+(y-m_y)^2}{2\sigma^2}\right)^2 dxdy$$

$$= \frac{1}{4\pi\sigma^2}$$

In addition Mathematical Expression 28 represents the latter half of the denominator in Mathematical Expression 9.

[Mathematical Expression 28]

$$\iint g(x,y)^2 dxdy = \iint \frac{1}{(2\pi a_x a_y \sigma^2)^2} \exp\left(-\frac{(x-a_x m_x - b_x)^2/a_x^2 + (y-a_y m_y - b_y)^2/a_y^2}{2\sigma^2}\right)^2 dxdy$$

$$= \frac{1}{4\pi a_x a_y \sigma^2}$$

Therefore Mathematical Expression 29 can represent the denominator in Mathematical Expression 9.

[Mathematical Expression 29]

$$\sqrt{\iint f(x,y)^2 dxdy} \ \sqrt{\iint g(x,y)^2 dxdy} = \frac{1}{4\pi\sigma^2 \sqrt{a_x a_y}}$$

Mathematical Expression 30 can represent the numerator in Mathematical Expression 9 from Mathematical Expressions and 23. Here, when $C_1$ and $C_2$ are set to Mathematical Expression 31, the numerator is represented as shown in Mathematical Expression 32.

[Mathematical Expression 30]

$$\iint f(x,y) g(x,y) dxdy = \iint \frac{1}{2\pi\sigma^2} \exp\left(-\frac{(x-m_x)^2+(y-m_y)^2}{2\sigma^2}\right) \cdot$$

$$\frac{1}{2\pi a_x a_y \sigma^2} \exp\left(-\frac{(x-a_x m_x - b_x)^2/a_x^2 + (y-a_y m_y - b_y)^2/a_y^2}{2\sigma^2}\right) dxdy$$

$$= \frac{1}{2\pi a_x \sigma^2} \int \exp\left(-\frac{(a_x^2(x-m_x)^2 + (x-am_x-b_x)^2)}{2a_x^2\sigma^2}\right) dx \cdot$$

$$\frac{1}{2\pi a_y \sigma^2} \int \exp\left(-\frac{(a_y^2(y-m_y)^2 + (y-am_y-b_y)^2)}{2a_y^2\sigma^2}\right) dy$$

[Mathematical Expression 31]

$$C_1 = \exp\left(-\frac{(a_x m_x + b_x - m_x)^2}{2(a_x^2+1)\sigma^2}\right)$$

$$C_2 = \exp\left(-\frac{(a_y m_y + b_y - m_y)^2}{2(a_y^2+1)\sigma^2}\right)$$

[Mathematical Expression 32]

$$\frac{C_1}{\sqrt{2\pi}\ \sigma\sqrt{a_x^2+1}} \cdot \frac{C_2}{\sqrt{2\pi}\ \sigma\sqrt{a_y^2+1}} = \frac{C_1 C_2}{2\pi\sigma^2\sqrt{a_x^2+1}\ \sqrt{a_y^2+1}}$$

Consequently Mathematical Expression 9 is represented by Mathematical Expression 33, which is the same in the case of one-dimension.

[Mathematical Expression 33]

$$\delta = \frac{2\sqrt{a_x a_y}}{\sqrt{a_x^2+1}\sqrt{a_y^2+1}} \exp\left(-\frac{(a_x m_x + b_x - m_x)^2/(a_x^2+1) + (a_y m_y + b_y - m_y)^2/(a_y^2+1)}{2\sigma^2}\right)$$

When the transfer and the change in sensitivity is considered like in the case of one-dimension, Mathematical Expression 34 represents the degree of similarity $\delta$ in the case of transfer ($a_x = a_y = 1$).

[Mathematical Expression 34]

$$\delta = \exp\left(-\left(\frac{b_x^2}{4\sigma^2} + \frac{b_y^2}{4\sigma^2}\right)\right)$$

In the case of the change in sensitivity ($b_x = b_y = 0$), Mathematical Expression 35 represents the degree of similarity $\delta$.

[Mathematical Expression 35]

$$\delta = \exp\left(-\left(\frac{(a_x-1)^2 m_x^2}{2(a_x^2+1)\sigma^2} + \frac{(a_y-1)^2 m_y^2}{2(a_y^2+1)\sigma^2}\right)\right)$$

Thus when two-dimension distributions f (x, y) and g (x, y) become more and more distant, the degree of similarity $\delta$ rapidly decreases. Needless to say, the same thing holds true of three-dimension distribution.

Figure 7A:
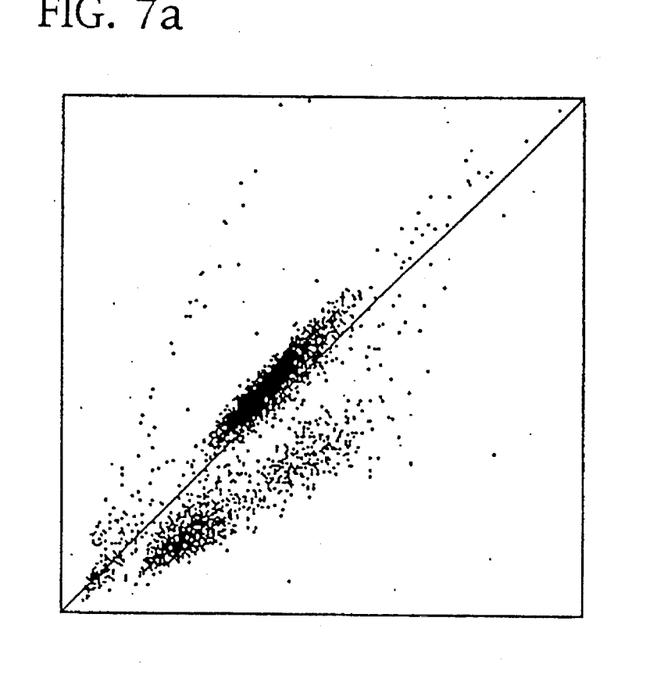
FIGS. 7a and 7b are views showing two-dimension distribution data obtained in the analysis with the particle analyzing apparatus in accordance with the present invention.
Figure 7B:
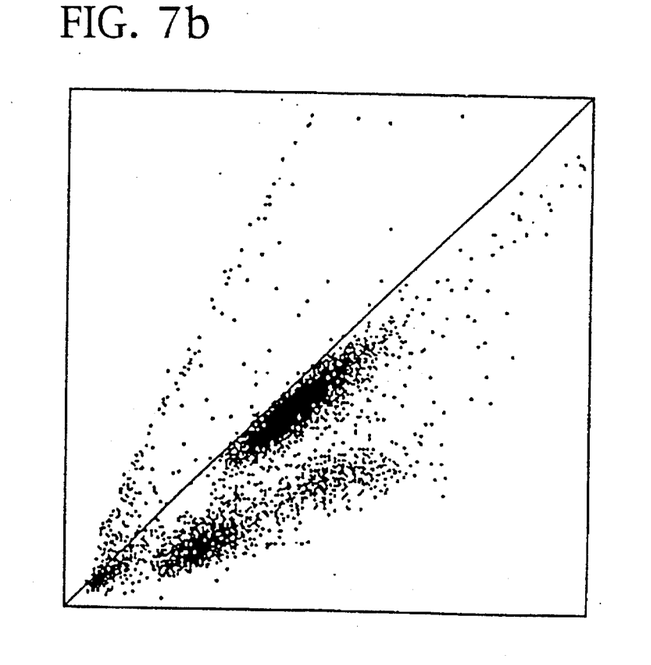

Therefore determination of the degree of similarity $\delta$ clarifies a difference between two distributions whose position cannot be easily differentiated without drawing a diagonal line shown in FIGS. 7a and 7b.

Figure 8:
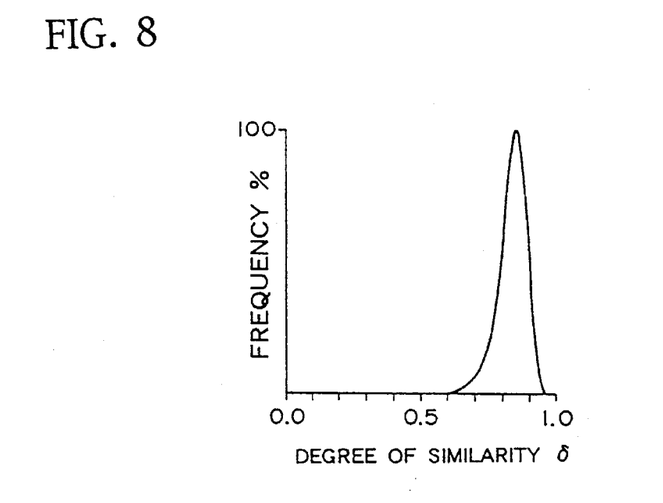
FIG. 8 is a view showing the result of inspection on the degree of similarity between particle size distributions with respect to two-dimension distribution data of leukocytes analyzed with a preferred Embodiment of a particle analyzer.

FIG. 8 shows a degree of similarity $\delta$ between two-dimension distribution data (the number of data items is represented by the formula; $100C_2 = 4950$) on leukocytes, which data item is obtained by analyzing with a particle analyzing apparatus of the present invention blood samples taken from 100 men in good health. A degree of similarity $\delta$ among healthy men is concentrated on 0.8 to 0.9 whereas a degree of similarity $\delta$ between healthy samples and unhealthy samples assumes a value lower than 0.8 to 0.9 described above. However the degree of the value depends on samples.

When the particle analyzing apparatus is used as an aid for diagnosis, the data base memory means 26 stores a typical distribution data item Gi in each disease and the name of each disease corresponding to the distribution data item Gi. In other words, typical distribution data is stored with respect to each disease. Each typical distribution data item Gi (case distribution data item) is obtained through the analysis of samples suffering from a disease which is already identified with a particle analyzing apparatus, and the distribution data items thus obtained are stored in the data base memory means 26 without processing them.

Then the distribution data item obtained in the measurement is compared with each case distribution data item stored in the data base memory means 26 to determine a degree of similarity $\delta$ between them. Then the name of diseases corresponding to the case distribution data item Gi exhibiting a large value of the degree of similarity $\delta$ is displayed on the display unit 20 as new inspection data along with the result of the measurement.

A large value of the degree of similarity $\delta$ indicates that the measured distribution data item is similar to the case distribution data item Gi compared with the former data item. Thus we can determine that the measured sample is very likely to correspond to the case i. Thus storing each kind of case distribution data item Gi in the data base memory means 26 enables retrieving cases from the measured distribution data.

Then it is still further possible to obtain more accurate degree of similarity $\delta$ with respect to each disease by preparing a plurality of case distribution data items such as Gi1, Gi2 and Gi3 with respect to one case i so that plural degrees of similarity $\delta i1$, $\delta i2$ and $\delta i3$ between the measured distribution data items and each case distribution data item Gi1, Gi2 and Gi3 are calculated and an average value thereof represented by $\delta i = (\delta i1 + \delta i2 + \delta i3)/3$ is further determined.

For quality control, the data base memory means 26 can store as basic distribution data one distribution data item obtained by measuring with a particle analyzing apparatus in a normal condition a material for quality control. For example, the material for quality control is measured every day before the onset of the analysis using the particle analyzing apparatus to obtain distribution data. This particular distribution data is compared with the above basic distribution data to calculate a degree of similarity $\delta$. Thus determination as to whether or not the degree of similarity $\delta$ exceeds a predetermined value or not allows determining whether the particle analyzing apparatus can function properly with a sufficient accuracy. This enables the control of the quality of the apparatus. Incidentally when the degree of similarity $\delta$ is smaller than the predetermined value, the display unit 20 displays a warning It is still further possible to detect the change in the quality of the particle analyzing apparatus with the passage of days by analyzing the material for quality control every day and calculating the degree of similarity $\delta$. In addition, the data base memory means 26 can store a plurality of distribution data items G1, G2 and G3 as basic distribution data with respect to the material for quality control. Then degrees of similarity $\delta 1$, $\delta 2$ and $\delta 3$ between the measured distribution data and the above basic distribution data are calculated and an average value of the above degrees of similarity $\delta$ is calculated so that the average value is set as the degree of similarity $\delta$. Thus more accurate value of $\delta$ can be obtained in the above process. Consequently use of the degree of similarity $\delta$ allows an quality control of this particle analyzing apparatus.

Furthermore when this particle analyzing apparatus is used in the inspection performed as part of the production process of the apparatus, the data base memory means 26 can store the reference distribution data G obtained when the particle analyzing apparatus measures in the normal operation a certain material for standard control. The above material for standard control is actually measured to give distribution data. Then a degree of similarity $\delta$ is calculated with respect to the above reference distribution data. A plurality of measurements are made of the material for quality control to observe to what extent the degree of similarity $\delta$ is reproduced in each measurement (to what extent the degree of similarity $\delta$ in each measurement is the same as the original degree of similarity $\delta$). This enables the detection of the reproducibility of distribution data and even the reproducibility of the particle analyzing apparatus.

It is still further possible to simply know the temperature stability of the distribution data and even the particle analyzing apparatus by measuring the above material for standard control to obtain distribution data and to calculate the degree of similarity δ under various temperatures so that change of the degree of similarity δ with the change in these temperatures can be observed. Thus the performance of the particle analyzing apparatus can be evaluated by observing the degree of similarity δ.

Although in the above Embodiment two kinds of data items were obtained from one particle, still larger number of data items may be obtained from the particle. Otherwise at least one kind of data item may be obtained from one particle. In such case the data conversion means 22 may classify one kind of data item into a proper rank to determine a histogram.

As described above, a particle analyzing apparatus and a method using the apparatus according to the present invention allows obtaining, as a numerical value, a degree of similarity δ of the distribution data obtained in the measurement with respect to the preliminarily determined reference distribution data by comparing the measurement distribution data with the reference distribution data. Therefore the present invention enables a quantitative evaluation of distribution data which has previously been determined only on the basis of subjective judgment of man who tends to see only part of a large amount of information contained in the distribution data. In particular, the present invention allows quantitatively performing diagnosis of diseases, and or quality control and evaluation of the particle analyzing apparatus.

What is claimed is:

1. A particle analyzing apparatus for analyzing particles in a fluid comprising:

particle detection means for measuring at least one physical characteristic of each of a plurality of particles in a fluid to obtain at least one data representative of each measured physical characteristic for each measured particle;

conversion means for converting the data obtained for the particles into distribution data;

data base storing means for storing reference distribution data;

calculation means for calculating a degree of similarity δ of the distribution data with respect to the reference distribution data; and display means for displaying the degree of similarity calculated by said calculation means.

2. A particle analyzing apparatus according to claim 1, wherein a number, n, of physical characteristics are measured for each particle, n being a positive integer equal to or greater than 1, the data representative of the n measured characteristics for each particle being defined by the set (X1 ... Xn), the distribution data being defined as F(X1 ... Xn), and the reference distribution data being defined as G(X1 ... Xn); and wherein said calculating means calculates the degree of similarity δ utilizing the expression:

$$\delta = \frac{\sum_{X1} \ldots \sum_{Xn} F(X1, \ldots XN) \cdot G(X1, \ldots Xn)}{\left( \sum_{X1} \ldots \sum_{Xn} |F(X1, \ldots Xn)|^2 \cdot \sum_{X1} \ldots \sum_{Xn} |G(X1, \ldots Xn)|^2 \right)^{1/2}}$$

for data in a predetermined region of the distribution data with respect to the reference distribution data.

3. A particle analyzing apparatus according to claim 1, wherein the particles are hemocytes and the reference distribution data are representative distribution data for a certain disease.

4. A particle analyzing apparatus according to claim 1, wherein the reference distribution data are distribution data obtained by measuring, with the particle analyzing apparatus, a material for quality control.

5. A particle analyzing apparatus according to claim 1, wherein the reference distribution data are distribution data obtained by measuring a material for quality evaluation.

6. A particle analyzing apparatus according to claim 1, wherein the particle detection means comprises:

a particle detector providing analog signals representative of the measured physical characteristics of each particle;

an amplifier circuit for amplifying the analog signals provided by the particle detector;

a waveform processing circuit for processing the amplified signals; and an A/D converter for converting the processed amplified signals into digital signals, the digital signals constituting the at least one data representative of the measured physical characteristic.

7. A particle analyzing apparatus according to claim 1, wherein the degree of similarity displayed by the display means comprises a numerical value.

8. A particle analyzing apparatus according to claim 1, wherein the degree of similarity displayed by the display means comprises a graph.

9. The particle analyzing apparatus of claim 1, wherein said particle detection means includes a flowcytometer having:

a light source directing light at the measured particles in the fluid; and a light detector for detecting light scattered by each particle as said at least one physical characteristic.

10. The particle analyzing apparatus of claim 9, wherein said flowcytometer further includes a fluorescence detector for detecting fluorescence generated by each particle as another of said physical characteristics.

11. The particle analyzing apparatus of claim 1, wherein the reference distribution data include a plurality of unique sets of reference distribution data, and wherein the calculation means calculates separate degrees of similarity of the distribution data for each of the plurality of unique sets of reference distribution data.

12. The particle analyzing apparatus of claim 11, wherein said calculation means averages the separate degrees of similarity to provide an average degree of similarity, and said display means displays the average degree of similarity calculated by the calculation means.

13. The particle analyzing apparatus of claim 11, wherein the plurality of unique sets of reference distribution data correspond to one certain disease.

14. The particle analyzing apparatus of claim 1, wherein the fluid is blood.

15. A particle analyzing apparatus according to claim 1, wherein said particle detection means includes a flowcytometer having:

a fine hole through which the particles pass;

an electric current supply means for supplying an electric current to the fine hole; and electric signal detector for detecting at least one electric signal as said at least one physical characteristic, the at least one electric signal being based on a change in impedance when the particles pass through the fine hole.

16. A particle analyzing apparatus according to claim 15, wherein said electric current supply means supplies a direct current and a high frequency current to the fine hole and said electric signal detector detects a first electric signal based on a change in the impedance of the direct current and a second electric signal based on a change in the impedance of the high frequency current when the particles pass through the fine hole. electric signal based on a change in the impedance of the high frequency current when the particles pass through the fine hole.

17. A method for analyzing particles in a fluid comprising the steps of:

(a) measuring at least one physical characteristic for each of a plurality of particles in a fluid to obtain at least one data representative of each measured physical characteristic for each particle;

(b) converting the data obtained for the particles into distribution data;

(c) storing reference distribution data;

(d) calculating a degree of similarity of the distribution data with respect to the reference distribution data.

18. A method for analyzing particles according to claim 17, wherein a number, n, of physical characteristics are measured for each particle, n being a positive integer equal to or greater than 1, the data representative of the n measured characteristics for each particle being defined by the set (X1 ... Xn), the distribution data being defined as F(X1 ... Xn), and the reference distribution data being defined as G(X1 ... Xn); and wherein said step (d) includes the step of calculating the degree of similarity δ includes the step of calculating the degree of similarity δ utilizing the expression:

$$\delta = \frac{\sum_{X1} \ldots \sum_{Xn} F(X1, \ldots XN) \cdot G(X1, \ldots Xn)}{\left( \sum_{X1} \ldots \sum_{Xn} |F(X1, \ldots Xn)|^2 \cdot \sum_{X1} \ldots \sum_{Xn} |G(X1, \ldots Xn)|^2 \right)^{1/2}}$$

for data in a predetermined region of the distribution data with respect to the reference distribution data.

19. The method for analyzing particles of claim 17, wherein said step (e) includes the step of displaying the degree of similarity as a numeral.

20. The method for analyzing particles of claim 17, wherein said step (e) includes the step of displaying the degree of similarity as a graph.

21. The method for analyzing particles of claim 17, wherein said step (a) is preceded by the steps of:

(A) providing blood as the fluid;

(B) diluting the blood; and (C) hemolyzing the blood.

22. A method for determining whether a particle analyzing apparatus is suitable for shipment as a product after being manufactured, comprising the steps of:

(a) providing a fluid having a plurality of particles suspended therein;

(b) measuring, using the particle analyzing apparatus immediately after its manufacture, at least one physical characteristic for individual particles in the fluid to obtain at least one data representative of each measured physical characteristic for the individual particles;

(c) converting the data obtained for the particles into distribution data;

(d) storing reference distribution data representing expected distribution data for the plurality of particles;

(e) calculating a degree of similarity of the distribution data relative to the reference distribution data;

(f) determining, on the basis of the calculated degree of similarity, whether the particle analyzing apparatus is suitable for shipment as a product.

23. The method of claim 22, wherein said step (d) further includes the steps of:

(e1) determining whether the calculated degree of similarity exceeds a predetermined value; and (e2) displaying a warning when the degree of similarity is smaller than the predetermined value; and wherein the determination of said step (f) is based upon whether the warning is displayed in said step (e2).

24. A method for evaluating the performance of a particle analyzing apparatus, comprising the steps of:

(a) performing a plurality of separate measurements on particles in a fluid using the particle analyzing apparatus, each measurement measuring at least one physical characteristic for individual particles in the fluid and obtaining at least one data representative of the measured physical characteristic for the individual particles, and wherein all of the separate measurements measure the same at least one physical characteristic;

(b) converting the data obtained for the particles into sets of distribution data, each set corresponding to a separate measurement;

(c) storing reference distribution data representing expected distribution data for the particles of the fluid;

(d) calculating a degree of similarity for each set of distribution data relative to the reference distribution data;

(e) displaying the calculated degree of similarity for each set of distribution data; and (f) evaluating, on the basis of the displayed degrees of similarity whether the performance of the particle analyzing apparatus is satisfactory.

25. The method of claim 24 for evaluating the performance of a particle analyzing apparatus, wherein each measurement of said step (a) is performed at a different temperature.

* * * * *